United States Patent
Li et al.

(10) Patent No.: US 8,738,150 B2
(45) Date of Patent: *May 27, 2014

(54) LEAD INCLUDING CONDUCTORS CONFIGURED FOR REDUCED MRI-INDUCED CURRENTS

(71) Applicant: Cardiac Pacemakers, Inc., St. Paul, MN (US)

(72) Inventors: Yingbo Li, Woodbury, MN (US); Masoud Ameri, Maple Plain, MN (US); G. Shantanu Reddy, Minneapolis, MN (US); Arthur J. Foster, Blaine, MN (US); James G. Bentsen, North St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/952,605

(22) Filed: Jul. 27, 2013

(65) Prior Publication Data

US 2013/0310910 A1    Nov. 21, 2013

Related U.S. Application Data

(63) Continuation of application No. 13/665,429, filed on Oct. 31, 2012, now Pat. No. 8,498,719, which is a continuation of application No. 13/030,467, filed on Feb. 18, 2011, now Pat. No. 8,326,436.

(60) Provisional application No. 61/306,377, filed on Feb. 19, 2010.

(51) Int. Cl.
*A61N 1/00*    (2006.01)

(52) U.S. Cl.
USPC .......................................................... 607/115

(58) Field of Classification Search
USPC .......................................................... 607/115
See application file for complete search history.

(56) References Cited

U.S. PATENT DOCUMENTS

| | | | |
|---|---|---|---|
| 5,545,207 | A | 8/1996 | Smits et al. |
| 6,038,472 | A | 3/2000 | Williams et al. |
| 6,104,961 | A | 8/2000 | Conger et al. |
| 8,326,436 | B2 | 12/2012 | Li et al. |
| 8,498,719 | B2 | 7/2013 | Li et al. |

(Continued)

FOREIGN PATENT DOCUMENTS

| | | |
|---|---|---|
| WO | WO2008115383 A2 | 9/2008 |
| WO | WO2009100003 A1 | 8/2009 |

OTHER PUBLICATIONS

International Search Report and Written Opinion issued in PCT/2011/025457, mailed Apr. 27, 2011, 13 pages.

*Primary Examiner* — Robert N Wieland
(74) *Attorney, Agent, or Firm* — Faegre Baker Daniels LLP

(57) ABSTRACT

An implantable medical device lead includes an inner conductor coil comprising one or more generally cylindrically wound filars. The inner conductor coil is configured to have a first inductance value greater than or equal to 0.2 µH/inch when the inner conductor coil is subjected to a range of radio frequencies. The implantable medical device lead also includes a multi-filar outer coil comprising two or more generally cylindrically wound filars. The multi-filar outer coil is configured to have a second inductance value greater than or equal to 0.1 µH/inch when the multi-filar outer coil is subjected to the range of radio frequencies.

20 Claims, 8 Drawing Sheets

(56) References Cited

U.S. PATENT DOCUMENTS

| | | |
|---|---|---|
| 2005/0197677 A1* | 9/2005 | Stevenson ................ 607/36 |
| 2005/0222657 A1 | 10/2005 | Wahlstrand et al. |
| 2006/0229693 A1 | 10/2006 | Bauer et al. |
| 2007/0179577 A1 | 8/2007 | Marshall et al. |
| 2008/0243218 A1 | 10/2008 | Bottomley et al. |
| 2009/0149920 A1 | 6/2009 | Li et al. |
| 2009/0198314 A1 | 8/2009 | Foster et al. |
| 2009/0270956 A1 | 10/2009 | Vase et al. |
| 2011/0208280 A1 | 8/2011 | Li et al. |
| 2013/0060314 A1 | 3/2013 | Li et al. |

* cited by examiner

LEAD INCLUDING CONDUCTORS CONFIGURED FOR REDUCED MRI-INDUCED CURRENTS

CROSS-REFERENCE TO RELATED APPLICATION

This application is a continuation of U.S. patent application Ser. No. 13/665,429, filed Oct. 31, 2012, which is a continuation of U.S. patent application Ser. No. 13/030,467, now U.S. Pat. No. 8,326,436, filed Feb. 18, 2011, which claims the benefit of Provisional Application No. 61/306,377, filed Feb. 19, 2010, which are incorporated herein by reference in their entirety.

TECHNICAL FIELD

Various embodiments of the present invention generally relate to implantable medical devices. More specifically, embodiments of the present invention relate to conductor configurations for magnetic resonance imaging (MRI) compatibility.

BACKGROUND

When functioning properly, the human heart maintains its own intrinsic rhythm and is capable of pumping adequate blood throughout the body's circulatory system. However, some individuals have irregular cardiac rhythms, referred to as cardiac arrhythmias, which can result in diminished blood circulation and cardiac output. One manner of treating cardiac arrhythmias includes the use of a pulse generator, such as a pacemaker, an implantable cardioverter defibrillator (ICD), or a cardiac resynchronization (CRT) device. Such devices are typically coupled to a number of conductive leads having one or more electrodes that can be used to deliver pacing therapy and/or electrical shocks to the heart. In atrioventricular (AV) pacing, for example, the leads are usually positioned in a ventricle and atrium of the heart, and are attached via lead terminal pins to a pacemaker or defibrillator which is implanted pectorally or in the abdomen.

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue. In some cases, imaging a patient's chest area may be clinically advantageous. In a chest MRI procedure, implanted pulse generators and leads may also be exposed to the applied electromagnetic fields.

SUMMARY

Various embodiments of the present disclosure generally relate to implantable lead conductor configurations for magnetic resonance imaging (MRI) compatibility.

In Example 1, an implantable medical device lead includes an inner conductor coil comprising one or more generally cylindrically wound filars. The inner conductor coil is configured to have a first inductance value greater than or equal to 0.2 pH/inch when the inner conductor coil is subjected to a range of radio frequencies. The implantable medical device lead also includes a multi-filar outer coil comprising two or more generally cylindrically wound filars. The multi-filar outer coil is configured to have a second inductance value greater than or equal to 0.1 µH/inch when the multi-filar outer coil is subjected to the range of radio frequencies.

In Example 2, the implantable medical device according to Example 1, wherein a layer of insulation is disposed about at least a portion of the inner conductor coil.

In Example 3, the implantable medical device according to either Example 1 or Example 2, wherein the inner conductor coil has a unifilar construction.

In Example 4, the implantable medical device according to any of Examples 1-3, wherein the inner conductor coil has an average pitch of approximately 0.005 inches.

In Example 5, the implantable medical device according to any of Examples 1-4, wherein the inner conductor coil has a unifilar construction and a mean coil diameter of 0.023 inches.

In Example 6, the implantable medical device according to any of Examples 1-5, wherein the inner conductor coil has an inductance greater than approximately 0.5 µH/inch.

In Example 7, the implantable medical device according to any of Examples 1-6, wherein the first inductance value (L) is set by a number of cylindrically wound filars (N), a pitch (b) of the inner conductor coil, and a mean coil diameter (a) by the equation $$L \approx \frac{\mu_0 \pi a^2}{4 b^2 N^2}$$

where µ0 is the permeability of the free space.

In Example 8, the implantable medical device according to any of Examples 1-7, wherein the inner conductor coil has a DC resistance less than 200 ohms.

In Example 9, the implantable medical device according to any of Examples 1-8, wherein the multi-filar outer coil is a ribbon-type conductor coil.

In Example 10, a medical lead includes a flexible body having a proximal region with a proximal end, and a distal region. A connector coupled to the proximal end of the body is configured for electrically and mechanically connecting the lead to an implantable pulse generator. An inner conductor coil is configured to convey electrical signals between a distal section and a proximal section of the lead, and the low voltage inner conductor coil includes one or more generally cylindrically wound filars. The inner conductor coil is configured to have a first inductance greater than or equal to 0.2 µH/inch when subjected to radio frequencies between 40 megahertz (MHz) and 300 MHz. A multi-filar outer conductor coil including two or more generally cylindrically wound filars radially surround at least a portion of the low voltage inner conductor coil. The multi-filar outer conductor coil is configured to have a second inductance greater than or equal to 0.1 µH/inch when subjected to the radio frequencies between 40 megahertz (MHz) and 300 MHz.

In Example 11, the medical lead according to Example 10, and further comprising a tri-filar shocking coil with a proximal end, wherein the proximal end of the tri-filar shocking coil is connected via a coupler to a distal end of the multi-filar outer coil.

In Example 12, the medical lead according to Example 11, wherein the multi-filar outer coil has an outer diameter larger than an outer diameter of the tri-filar shocking coil.

In Example 13, the medical lead according to any of Examples 10-12, wherein the multi-filar outer conductor comprises a quad-filar coil having a helix-like shape.

In Example 14, the medical lead according to any of Examples 10-13, wherein the lead further includes one or more layers of insulating material surrounding one or both of the inner conductor coil and the multi-filar outer conductor coil.

In Example 15, the medical lead according to any of Examples 10-14, wherein the inner conductor coil and the multi-filar outer conductor coil have different pitches.

In Example 16, the medical lead according to any of Examples 10-15, wherein the inner conductor coil and the multi-filar outer conductor coil each have a pitch no greater than about 0.005 inch (0.127 mm).

In Example 17, an implantable medical device lead includes an inner conductor coil comprising one or more wound filars and configured to have a first inductance value greater than or equal to 0.2 µH/inch when subjected to radio frequencies between 40 megahertz (MHz) and 300 MHz. The implantable medical device lead also includes a multi-filar outer conductor coil comprising two or more generally cylindrically wound filars radially surrounding at least a portion of the inner conductor coil and configured to have a second inductance value greater than 0.1 µH/inch when subjected to the radio frequencies between 40 megahertz (MHz) and 300 MHz. The implantable medical device lead further includes a tri-filar shocking coil with a proximal end, wherein the proximal end is connected via a coupler to a distal end of the multi-filar outer conductor coil.

In Example 18, the implantable medical device according to Example 17, wherein the inner conductor coil, the multi-filar outer conductor coil, and the tri-filar shocking coil have different pitches.

In Example 19, the implantable medical device according to either Example 17 or Example 18, wherein the lead further includes one or more layers of insulating material surrounding one or more of the low voltage inner conductor coil, the multi-filar high voltage outer conductor coil, and the tri-filar shocking coil.

In Example 20, the implantable medical device according to any of Examples 17-19, wherein a pitch of the multi-filar outer conductor coil is about 0.010 inches, a mean coil diameter of the multi-filar outer conductor coil is about 0.090 inches and results in a coil inductance value of about 0.13 µH/inch, and a pitch of the inner conductor coil is about 0.005 inches, the inner conductor coil is formed from one cylindrically wound filar, and a mean coil diameter of the inner conductor coil is about 0.023 inches resulting in a coil inductance per unit length value of about 0.5 µH/inch.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
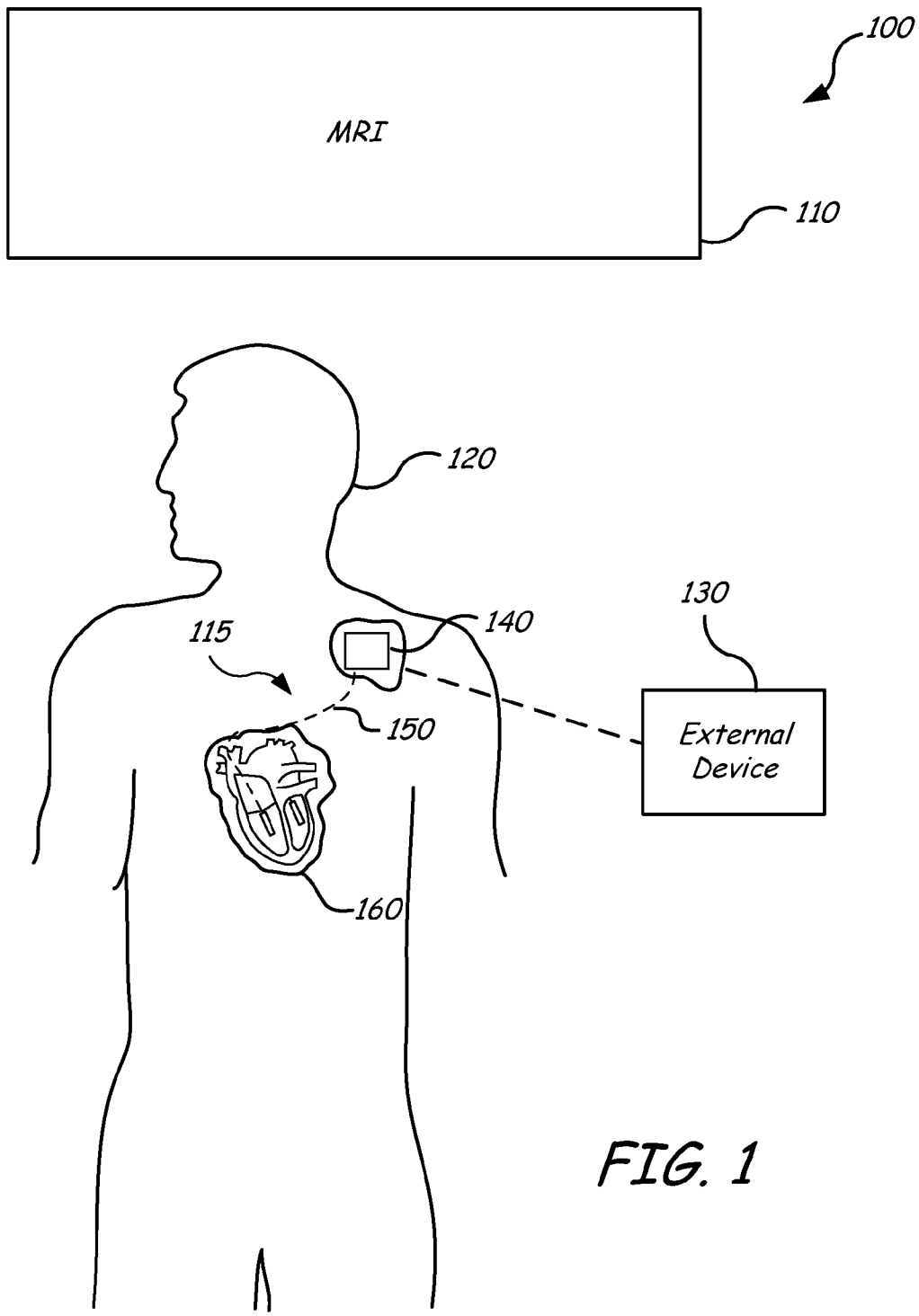
FIG. 1 is a schematic illustration of a medical system including an MRI scanner, and an implantable cardiac rhythm management system implanted within a torso of a human patient according to various embodiments of the present invention.

The drawings have not necessarily been drawn to scale. For example, the dimensions of some of the elements in the figures may be expanded or reduced to help improve the understanding of the embodiments of the present invention. While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable cardioverter defibrillator (ICD) is typically implanted in the pectoral region of a patient. In some cases, one or two electrodes may extend from the ICD into an atrium and/or ventricle of the patient's heart. In the case of epicardial leads, the electrodes are attached to an external surface of the patient's heart. The ICD system can provide pacing capability to the patient's heart and/or a high voltage shocking therapy to convert patient's heart from fibrillation to normal heart function.

As explained in further detail below, various embodiments of the present invention relate to new lead designs advantageously adapted for operation in a magnetic resonance imaging (MRI) environment. In some embodiments, the leads include combinations of unique shocking coils and/or coil conductors configured to provide suitable electrical performance for tachycardia therapy and also to minimize the lead's reaction to applied electromagnetic energy during MRI procedures.

In the following description, for the purposes of explanation, numerous specific details are set forth in order to provide a thorough understanding of embodiments of the present invention. It will be apparent, however, to one skilled in the art that embodiments of the present invention may be practiced without some of these specific details.

While, for convenience, some embodiments are described with reference to ICDs in the presence of MRI scanners. Embodiments of the present invention may be applicable to various other physiological measurements, treatments, implantable medical devices, and other non-invasive examination techniques in which conductive leads are exposed to time varying magnetic fields. As such, the applications discussed herein are not intended to be limiting, but instead exemplary. Other systems, devices, and networks to which embodiments are applicable include, but are not limited to, other types of sensory systems, medical devices, medical treatments, and computer devices and systems. In addition, various embodiments are applicable to all levels of sensory devices from a single IMD with a sensor to large networks of sensory devices.

FIG. 1 is a schematic illustration of a medical system 100 including a MRI scanner 110, an implantable cardiac rhythm management (CRM) system 115 implanted within a torso of a human patient 120, and one or more external device(s) 130 according to various embodiments. The external device(s) 130 are capable of communicating with the CRM system 115 implanted within the patient 120. In the embodiment shown in FIG. 1, the CRM system 115 includes a pulse generator (PG) 140 and a lead 150. During normal device operation, the PG 140 is configured to deliver electrical therapeutic stimulus to the patient's heart 160 for providing tachycardia ventricular fibrillation, anti-bradycardia pacing, anti-tachycardia pacing, and/or other types of therapy.

Thus, in the illustrated embodiment, the PG 140 can be a device such as an ICD, cardiac resynchronization therapy device with defibrillation capabilities (a CRT-D device), or a comparable device. The PG 140 can be implanted pectorally within the body, typically at a location such as in the patient's chest. In some embodiments, PG 140 can be implanted in or near the abdomen.

The external devices 130 may be a local or remote terminal or other device (e.g., a computing device and/or programming device), operable to communicate with the PG 140 from a location outside of the patient's body. According to various embodiments, external device 130 can be any device external to the patient's body that is telemetry enabled and capable of communicating with the PG 140. Examples of external devices can include, but are not limited to, programmers (PRM), in-home monitoring devices, personal computers with telemetry devices, MRI scanner with a telemetry device, manufacturing test equipment, or wands. In some embodiments, the PG 140 communicates with the remote terminal 130 via a wireless communication interface. Examples of wireless communication interfaces can include, but are not limited to, radio frequency (RF), inductive, and acoustic telemetry interfaces.

Figure 2A:
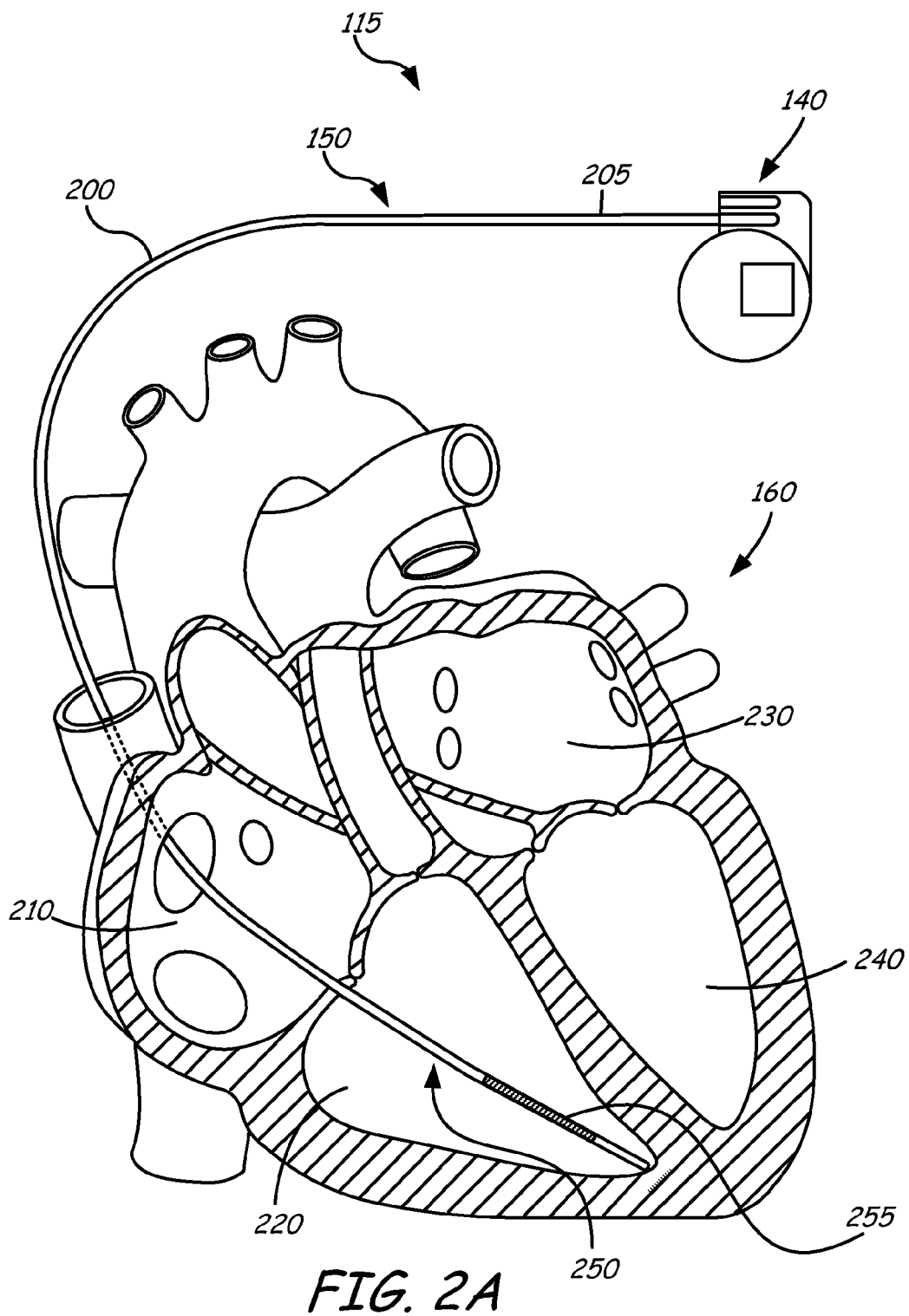
FIG. 2A is a schematic view of an illustrative pulse generator and lead implanted within the body of a patient which may be used in accordance with some embodiments of the present invention.

FIG. 2A is a more detailed schematic view of the CRM system 115 including the illustrative PG 140 equipped with the lead 150 implanted within the body of a patient. In the embodiments depicted, CRM system 115 includes a PG implanted near the patient's heart 160 and lead 150 having a distal portion implanted with the patient's heart 160. As can be seen in FIG. 2A, the heart 160 includes a right atrium 210, a right ventricle 220, a left atrium 230, and a left ventricle 240.

The lead 150 has a flexible body 200 including a proximal region 205 and a distal region 250. As shown, the lead 150 is coupled to the PG 140, and the distal region 250 of the lead body 200 is at least partially implanted at a desired location within the right ventricle 220. As further shown, the lead 150 includes at least one electrode 255 along the distal region 250, such that when implanted as shown in FIG. 2A, it is positioned within the right ventricle 220. As explained and illustrated in further detail below, the lead 150 includes one or more electrical conductor coils within the lead body 250 (not visible in FIG. 2A) electrically coupling the electrode 255 to circuitry and other electrical components within the PG 140 for transmitting intrinsic cardiac signals from the heart 160 to the PG 140 and also for transmitting electrical shocks or low-voltage pacing stimuli to the heart 160 via the electrode 255.

Although the illustrative embodiment depicts only a single lead 150 inserted into the patient's heart 160, in other embodiments multiple leads can be utilized so as to electrically stimulate other areas of the heart 160. In some embodiments, for example, the distal portion of a second lead (not shown) may be implanted in the right atrium 210. In addition, or in lieu, another lead may be implanted at the left side of the heart 160 (e.g., in the coronary veins, the left ventricle, etc.) to stimulate the left side of the heart 160. Other types of leads such as epicardial leads may also be utilized in addition to, or in lieu of, the lead 150 depicted in FIGS. 1-2.

During operation, the lead 150 conveys electrical signals between the heart 160 and the PG 140. For example, in those embodiments where the PG 140 has pacing capabilities, the lead 150 can be utilized to deliver electrical therapeutic stimulus for pacing the heart 160. In those embodiments where the PG 140 is an ICD, the lead 150 can be utilized to deliver high voltage electric shocks to the heart 160 via the electrode 255 in response to an event such as a ventricular fibrillation. In some embodiments, the PG 140 includes both pacing and defibrillation capabilities.

Figure 2B:
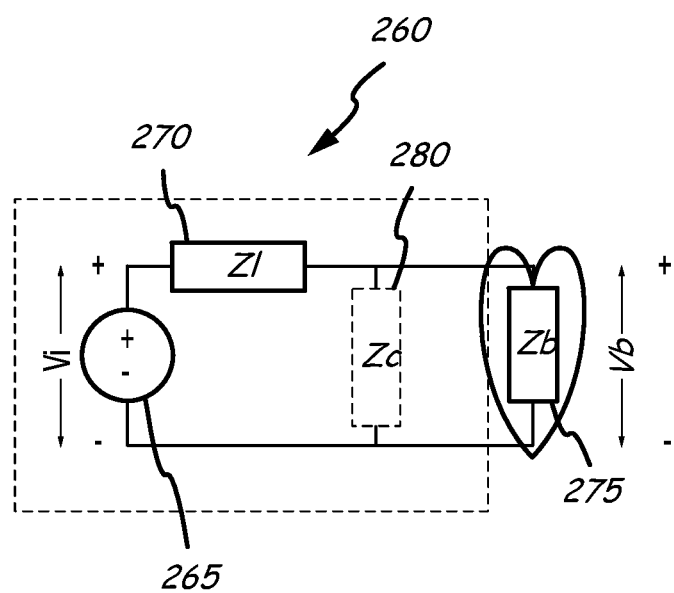
FIG. 2B is a schematic view showing a simplified equivalence circuit for the lead of FIG. 2A

FIG. 2B is a schematic view showing a simplified equivalence circuit 260 for the lead 150 of FIG. 2A, representing the RF energy picked up on the lead 150 from RF electromagnetic energy produced by an MRI scanner. As shown in FIG. 2B, voltage (Vi) 265 in the circuit 260 represents an equivalent source of energy picked up by the lead 150 from the MRI scanner. During magnetic resonance imaging, the length of the lead 150 functions similar to an antenna, receiving the RF energy that is transmitted into the body from the MRI scanner. Voltage (Vi) 265 in FIG. 2B may represent, for example, the resultant voltage received by the lead 150 from the RF energy. The RF energy picked up by the lead 150 may result, for example, from the rotating RF magnetic field produced by an MRI scanner, which generates an electric field in the plane perpendicular to the rotating magnetic field vector in conductive tissues. The tangential components of these electric fields along the length of the lead 150 couple to the lead 150. The voltage (Vi) 265 is thus equal to the integration of the tangential electric field (i.e., the line integral of the electric field) along the length of the lead 150.

The ZI parameter 270 in the circuit 260 represents the equivalent impedance exhibited by the lead 150 at the RF frequency of the MRI scanner. The impedance value ZI 270 may represent, for example, the inductance or the equivalent impedance resulting from the parallel inductance and the coil turn by turn capacitance exhibited by the lead 150 at an RF frequency of 64 MHz for a 1.5 Tesla MRI scanner, or at an RF frequency of 128 MHz for a 3 Tesla MRI scanner. The impedance ZI of the lead 150 is a complex quantity having a real part (i.e., resistance) and an imaginary part (i.e., reactance).

Zb 275 in the circuit 260 may represent the impedance of the body tissue at the point of lead contact. Zc 280, in turn, may represent the capacitive coupling of the lead 150 to surrounding body tissue along the length of the lead 150, which may provide a path for the high frequency current (energy) to leak into the surrounding tissue at the RF frequency of the MRI scanner. Minimizing the absorbed energy (represented by source Vi 265) reduces the energy that is transferred to the body tissue at the point of lead contact with the body tissue.

As can be further seen in FIG. 2B, the lead 150 has some amount of leakage into the surrounding tissue at the RF frequency of the MRI scanner. As further indicated by 275, there is also an impedance at the point of contact of the lead electrode(s) 255 to the surrounding body tissue within the heart 160. The resulting voltage Vb delivered to the body tissue may be related by the following formula:

$$Vb = Vi\, Zbe/(Zbe+Zl), \text{ where } Zbe=Zb \text{ in parallel with } Zc.$$

The temperature at the tip of the lead 150 where contact is typically made to the surrounding tissue is related in part to the power dissipated at 275 (i.e., at "Zb"), which, in turn, is related to the square of Vb. To minimize temperature rises resulting from the power dissipated at 275, it is thus desirable to minimize Vi (265) and Zc (280) while also maximizing the impedance ZI (270) of the lead 150. In some embodiments, the impedance ZI (270) of the lead 150 can be increased at the RF frequency of the MRI scanner, which aids in reducing the energy dissipated into the surrounding body tissue at the point of contact 275.

In the various embodiments described in further detail below, the impedance of the lead 150 can be increased by adding inductance to the lead 150 and/or by a suitable construction technique. For example, in various embodiments, the inductance of the lead 150 is increased by increasing the mean diameter of the conductor coil(s) and/or by decreasing the pitch of the conductor coil(s) used to supply electrical energy to the electrode(s) 255. Decreasing the coil pitch may result in increasing capacitance between successive turns of the coil (i.e., coil turn by turn capacitance). The parallel combination of inductance (from the helical shape of the coil) and the turn by turn capacitance constitutes a resonance circuit. For a helically coiled lead construction, if the resonance frequency of the lead is above the RF frequency of the MRI, then the helical coil acts as an inductor. For an inductor, increasing the cross section of the coil area and/or reducing the coil pitch increases the inductance and, as a result, increases the impedance of the lead 150.

Figure 3:
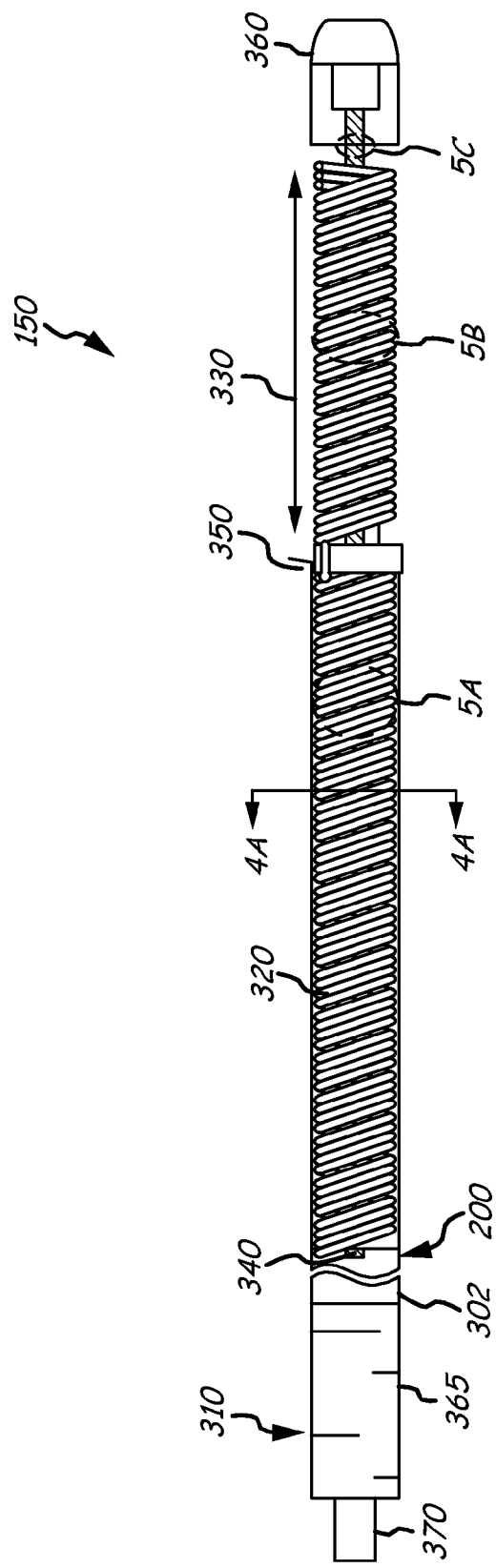
FIG. 3 illustrates an exemplary lead that may be used in accordance with one or more embodiments of the present invention.

FIG. 3 schematically illustrates in further detail the exemplary lead 150 that may be used in accordance with one or more embodiments of the present invention. In FIG. 3, a portion of the lead body 200 is shown partially cut-away to better illustrate the internal features of the lead 150. As shown in FIG. 3, the lead body 200 includes a proximal end 302, and the lead 150 further includes a connector assembly 310 coupled to the proximal end 302 of the lead body, a high voltage shocking conductor coil 320, a shocking coil 330, an inner conductor coil 340, a coupler 350, and pace/sense electrode 360. Depending on the functional requirements of the IMD 140 (see FIG. 1), and the therapeutic needs of the patient, the distal region may include additional shocking coils (not shown) and/or pace/sense electrodes. For example, in some embodiments, a pair of coil electrodes can be used to function as shocking electrodes for providing a defibrillation shock to the heart 160.

In the illustrated embodiment, the connector assembly 310 includes a connector body 365 and a terminal pin 370. The connector assembly 310 is coupled to the lead body and can be configured to mechanically and electrically couple the lead to a header on PG 140 (see FIG. 1). In various embodiments, the terminal pin 370 extends proximally from the connector body 365 and in some embodiments is coupled to the inner conductor coil 340 that extends longitudinally through the lead body 200 to the pace/sense electrode 360. In the illustrated embodiment, the pace/sense electrode 360 is a tip electrode located at the distal-most extremity of the lead 150, and is fixed relative to the lead body 200 such that the lead 150 is considered a passive-fixation lead. In other embodiments, the lead 150 may include additional pace/sense electrodes located more proximally along the lead 150. In some embodiments, the terminal pin 370 can include an aperture extending therethrough communicating with a lumen defined by the inner conductor coil 340 in order to accommodate a guide wire or an insertion stylet.

In some embodiments, the pace/sense electrode 360 may be in the form of an electrically active fixation helix at the distal end of the lead 150. In various such embodiments, the pace/sense electrode 360 can be an extendable/retractable helix supported by a mechanism to facilitate longitudinal translation of the helix relative to the lead body as the helix is rotated. In those embodiments, the terminal pin 370 may be rotatable relative to the connector body 365 and the lead body 200 such that rotation of the terminal pin 370 relative to the lead body 200 causes the inner conductor coil 340, and in turn, the helical pace/sense electrode 360 to rotate and translate longitudinally relative to the lead body 200. Various mechanisms and techniques for providing extendable/retractable fixation helix assemblies (both electrically active and passive) are known to those of ordinary skill in the art, and need not be described in greater detail here.

The pace/sense electrode 360 (whether a solid tip electrode such as shown in FIG. 3 or an active-fixation helix as described above) can be made of any suitable electrically conductive material such as Elgiloy, MP35N, tungsten, tantalum, iridium, platinum, titanium, palladium, stainless steel, as well as alloys of any of these materials.

The inner conductor coil 340 can be a relatively low voltage conductor to carry the pacing and sensing signal to and from the heart 160. Low voltage inner conductor coil 340 can be formed, according to various embodiments, from one or more generally cylindrically wound filars. As explained in further detail below, in some embodiments, the low voltage inner conductor coil 340 is configured to have an inductance value greater than or equal to 0.2 µH/inch to reduce the RF current induced in the inner conductor coil 340 due to an external MRI field, and also to prevent undesired high-rate stimulation of the heart. In some embodiments, the inductance value is around 0.5 µH/inch. Additionally, the inner conductor coil 340, in some embodiments, is configured to have a DC resistance less than 200 ohms.

In some embodiments, the high voltage conductor coil 320 can provide a high voltage path that can deliver up to 1000 volts and 40 J of energy to the patient's heart 160, as may be necessary for applying an anti-tachycardia shock. The high voltage conductor coil 320 is configured, in the various embodiments, to have a high inductance to reduce the current that induced by the RF pulses generated by an MRI device or other system. In some embodiments, the inductance is greater than or equal to 0.1 µH/inch. The outer diameter can be increased to make up for a loss of inductance in some embodiments. According to one or more embodiments, the high voltage conductor coil 320 may have a multi-filar construction to decrease the direct current (DC) resistance. In some embodiments, the DC resistance will be below approximately ten ohms (e.g., six or seven ohms in some embodiments), so that the maximum energy can be delivered to the heart.

In some embodiments, the high voltage coil 320 can be divided into two paths; one path can be connected to a shocking coil that is proximal to the ICD. Another path can be connected to a shocking coil that is distal to the ICD. The distal shocking coil, in conjunction with the high voltage coil 320, can serve as the returning path of the pacing pulse in bipolar pacing. Alternatively, a second high voltage path may be provided via a high voltage coil (not shown) separate from the high voltage coil 320.

In some embodiments, the high voltage conductor coil 320 is mechanically and electrically coupled to the shocking coil 330 via coupler 350. This path can also serve as the returning path of the pacing pulse in bipolar pacing. The shocking coil 330 can also deliver proper therapy to the patient's heart. Examples of therapy include, but are not limited to, tachycardia ventricular fibrillation, anti-bradycardia pacing, anti-tachycardia pacing, and/or other types of therapy.

In some embodiments, the shocking coil 330 may have a coating that is configured to control (i.e. promote or discourage) tissue in-growth. In various embodiments, the lead may include only a single coil electrode such as shocking coil 330. In other embodiments, the lead 150 may include one or more ring electrodes (not shown) along the lead body in lieu of or in addition to the shocking coil electrodes 330. When present, the ring electrodes may operate as relatively low voltage pace/sense electrodes. As will be appreciated by those skilled in the art, a wide range of electrode combinations may be incorporated into the lead 150 within the scope of the various embodiments of the present invention.

Figure 4:
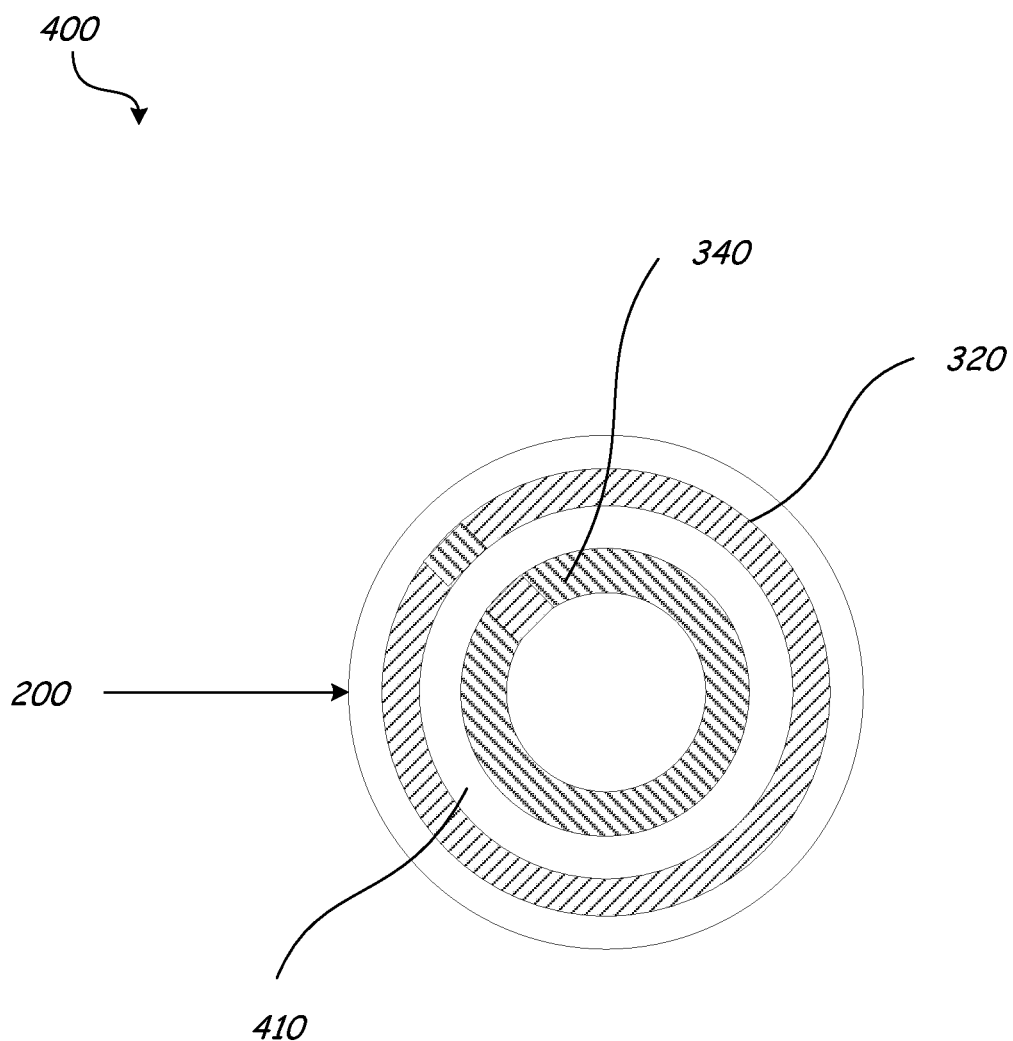
FIG. 4 illustrates a cross-sectional view of a high voltage shocking coil and a low voltage coil in accordance with various embodiments of the present invention.

FIG. 4 illustrates a cross-sectional view 400 of the lead 150 taken along the line 4A in FIG. 3. As shown in FIG. 4, in the illustrated embodiment, the high voltage conductor coil 320 and the low voltage inner conductor coil 340 are coaxially disposed within the lead body 200. As further shown, in the illustrated embodiment, the lead 150 includes an insulation layer 410 between the high voltage conductor coil 320 and the low voltage inner conductor coil 340 so as to electrically isolate these coils from one another. In various embodiments, the individual filars of the high voltage conductor coil 320 and/or the low voltage inner conductor coil 340 may be individually insulated in addition to or in lieu of using the insulation layer 410. Accordingly, in the embodiment shown in FIG. 4, the filars of the high voltage conductor coil 320 and the low voltage inner conductor coil 340 each have a thin layer of insulation. In other embodiments, the filars of the high voltage conductor coil 320 and/or the low voltage inner conductor coil 340 are not individually insulated, and are spaced apart to avoid contact with adjacent filars.

Figure 5A:
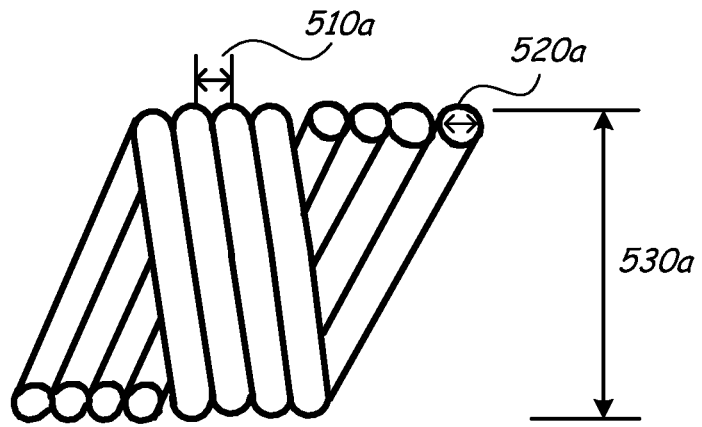
FIGS. 5A-5C show various portions of the inner conductor coil, the high voltage conductor coil, and the shocking coil according to some embodiments of the present invention.
Figure 5B:
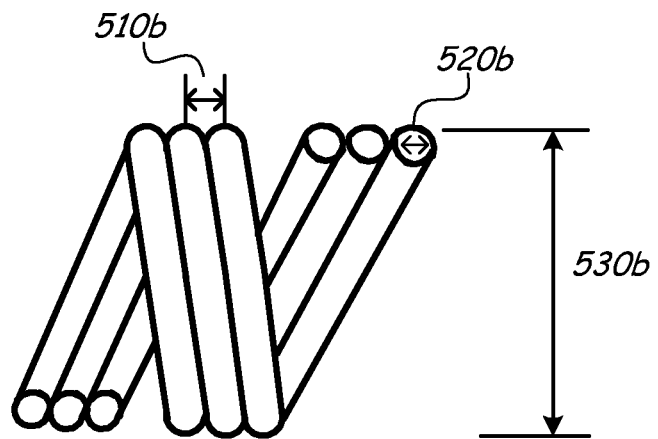
Figure 5C:
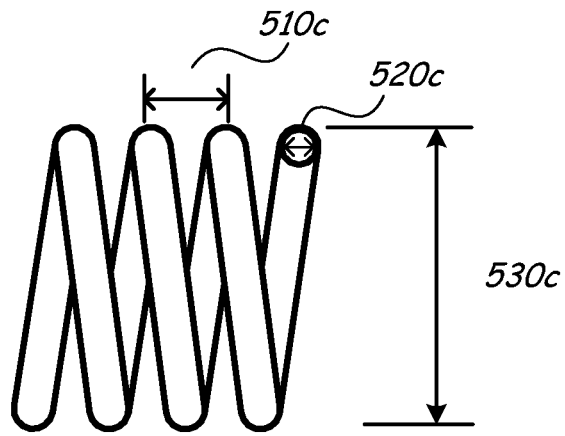

Examples of the types of insulation material that can be used in various embodiments of the present invention include, but are not limited to, silicone, polytetrafluoroethylene, expanded polytetrafluoroethylene, ethylene tetrafluoroethylene, and co-polymers of the foregoing. In some embodiments, the insulating layer of the individual filars can prevent the turns of the coil from coming in contact with each other when an uncoiled lead is placed in a helix configuration as shown in FIGS. 5A-5C. In addition, some embodiments include a sufficient insulation layer between the low voltage coil and high voltage coil to prevent electrical coupling.

As explained above, according to various embodiments of the present invention, the high voltage conductor coil 320 and/or the low voltage inner conductor coil 340 are selectively configured to have a high impedance to minimize the effects of applied MRI radiation without unduly impacting electrical performance under normal operating conditions (e.g., for providing anti-tachycardia therapy). As explained in further detail below, in various embodiments, the filar thickness, pitch, and/or mean coil diameter for the high voltage conductor coil 320 and/or the low voltage inner conductor coil 340 are selectively chosen to provide the desired balance of electrical operating performance and MRI-compatibility.

FIGS. 5A-5C show various configurations of the inner conductor coil 340, the high voltage conductor coil 320, and the shocking coil 330, respectively, according to some embodiments of the present invention. According to various embodiments, the pitch of a helix is the width of one complete helix turn, measured along the helix axis. Distances 510a-510c in FIGS. 5A-5C illustrate the pitch of the coils shown, reference numerals 520a-520c represent the filar thickness for the respective coils, and reference numeral 530a-530c represents the mean coil diameter. According to one or more embodiments, the pitch may be a constant pitch along the length of the lead (see, e.g., FIG. 5C) or follow a repeating pattern along the length of the lead (see, e.g., FIGS. 5A and 5B). In some embodiments, a ribbon type conductor may be used for the high voltage conductor coil 320 and the shocking coil 330. In some embodiments, the pitch directions for coils 320, 330, 340 are the same.

FIG. 5A illustrates a portion of the high voltage conductor coil 320 in accordance with some embodiments of the present invention. In the illustrated embodiment, the high voltage conductor coil 320 is a quad-filar coil. However, in one or more embodiments, the high-voltage multi-filar outer coil 320 can have other types of multi-filar constructions. The multi-filar construction of the high voltage conductor coil 320 results in a relatively low DC resistance, e.g., below approximately ten ohms and can be formed from two or more generally cylindrically wound filars. Such constructions allow the high voltage conductor coil 320 to be suitable for use in high voltage defibrillation lead applications.

In various embodiments, the high-voltage multi-filar outer coil can have a pitch 510a and a filar thickness 520a of various dimensions to result in a desired coil inductance value (e.g., greater than or equal to 0.2 µH/inch) when the high-voltage multi-filar outer coil 320 is subjected to an electromagnetic field at a range of radio frequencies (e.g., 40 MHz to 300 MHz) typical of an MRI scan. In some embodiments, the desired coil inductance value is around 0.5 µH/inch. As discussed above (e.g., see discussion of FIG. 2B), the impedance and inductance of lead 150 can be advantageously adjusted by the choice of various structural features of the lead. Examples of structural features include, but are not limited to, pitch 510a, filar thickness 520a, coil diameter 530a, and others.

For a typical cylindrically closely wound coil, the inductance of the coil per unit length can be approximated using the following equation:

$$L \approx \frac{\mu_0 \pi a^2}{4 b^2 N^2}$$

where $\mu_0$ is the permeability of the free space, a is the mean diameter of the coil 530a, b is the pitch of the coil 510a (i.e., distance between adjacent filars), and N is the filar count. Based on the equation, coil inductance per unit length is proportionally to the square of the radius, and reversely proportional to the square of the pitch and filar count.

FIG. 5B illustrates a portion of the high voltage shocking coil 330 in accordance with some embodiments of the present invention. In the illustrated embodiment, the high voltage shocking coil 330 is a tri-filar coil. However, in one or more embodiments, the high voltage shocking coil 330 can have other types of multi-filar constructions. The multi-filar construction of the high voltage shocking coil 330 results in a relatively low DC resistance and can be formed from two or more generally cylindrically wound filars. Such constructions allow the high voltage shocking coil 330 to be suitable for use in high voltage defibrillation lead applications.

In some embodiments, the third coil, i.e., shocking coil 330, can have a first end that is connected to the distal section of the high-voltage multi-filar outer coil 320 via coupler 350. The third coil 330 can be formed in some embodiments, from two or more generally cylindrically wound filars. According to various embodiments, the filar thickness, the pitch 510*b*, and the mean coil diameter 520*b* can be configured such that the shocking coil 330 has a high impedance value when the shocking coil 350 is subjected to an electromagnetic field at the range of radio frequencies (e.g., 40 MHz and 300 MHz) characteristic of an MRI scan. As discussed above (e.g., see discussion of FIG. 2B), the impedance and inductance of lead 150 can be advantageously adjusted by the choice of various structural features of the lead. Examples of structural features include, but are not limited to, pitch, filar thickness, coil diameter, and others.

FIG. 5C illustrates a portion of the low voltage inner coil 340 in accordance with some embodiments of the present invention. In the illustrated embodiment, the low voltage inner coil 340 is a uni-filar coil. However, in one or more embodiments, the low voltage inner coil 340 can have other types of multi-filar constructions (e.g., 2-filar, 3-filar, etc.). The uni-filar construction of low voltage inner coil 340 results in a higher DC resistance, e.g., of approximately two hundred ohms. Such constructions allow the low voltage inner coil 340 to be suitable for use in pacing applications.

In some embodiments, the inner conductor coil 340 can be split into two paths; one for cathode and one for anode for pacing pulses. In one embodiment, the inner conductor coil 340 has a pitch 510*c*, a filar thickness 520*c*, and a mean coil diameter 530*c* that result in a coil desired impedance value when the inner conductor coil 340 is subjected to the range of radio frequencies (e.g., 40 MHz and 300 MHz. As discussed above (e.g., see discussion of FIG. 2B), the impedance and inductance of lead 150 and/or lead coils can be advantageously adjusted by the choice of various structural features of the lead. Examples of structural features include, but are not limited to, pitch, filar thickness, coil diameter, and others.

In one embodiment, the high voltage conductor coil 320 has a pitch 510*a* of about 0.010 inches, four filar count, and a mean coil diameter 530*a* of about 0.050 inches, resulting in a coil inductance value of about 0.13 µH/inch. The lower limit for high voltage coil is thus set to be 0.1 be µH in one embodiment. The inner conductor coil 340 has a pitch 510*c* of about 0.005 inches, filar count of 1, and a mean coil diameter of about 0.023 inches, resulting in a coil inductance per unit length value of about 0.5 µH/inch in one embodiment. The lower limit for low voltage coil can be set to approximately 0.2 µH in some embodiments. In some embodiments, the low voltage coil and high voltage coil inductance limits can be different, while in other embodiments the inductance limits can be the same.

As discussed above, the designs of various embodiments of the present invention can result in significant heat reduction over normal lead designs when exposed to MRI related frequencies. In one exemplary embodiment, a test sample can have a uni-filar low voltage coil made from approximately 0.004 inches OD wire. The OD of the coil is approximately 0.027 inches and the pitch of the coil is close to 0.004 inches. The test sample further has a 4 filar high voltage coil, made from approximately 0.010 inch wire. The high voltage coil has an OD of approximately 0.090 inches and the pitch of the coil is approximately 0.012 inches.

Figure 6:
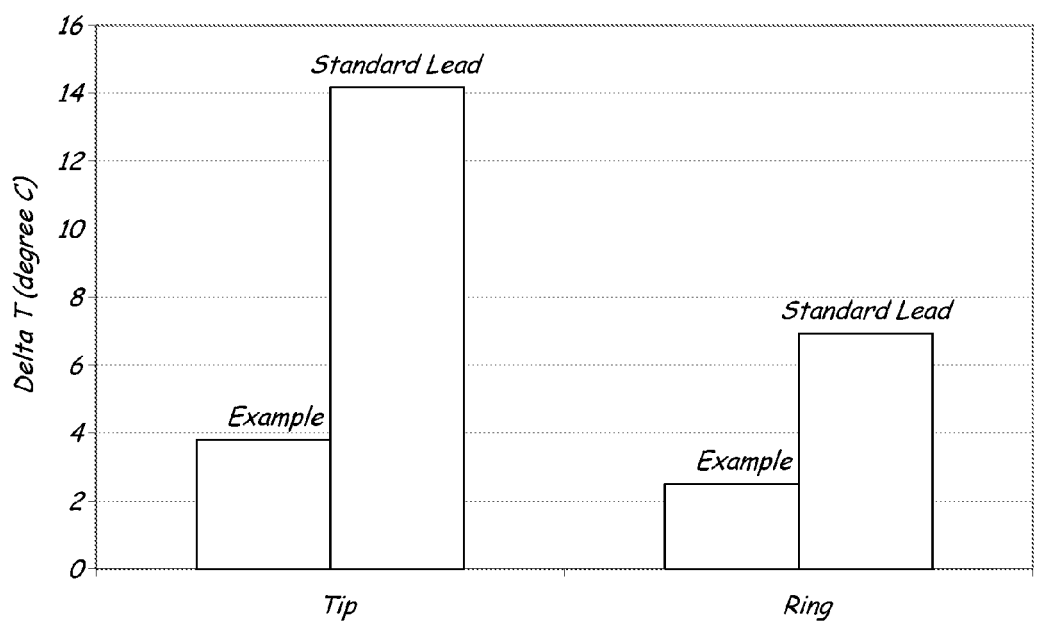
FIG. 6 illustrates an example of a resulting temperature increase when a standard lead design and an exemplary lead designed according to various embodiments of the present invention when the standard lead design and the exemplary lead design are subjected to MRI related frequencies.

FIG. 6 illustrates the resulting temperature increases when a standard lead design and the exemplary lead design is subjected to MRI related frequencies. The total test mule length is 60 cm. The heating tests for the standard lead design and the exemplary lead design were performed under the same 64 MHz testing conditions. As can be seen in FIG. 6, the exemplary lead design results in a temperature rise approximately ten degrees less than that of a standard lead at the tip. In addition, the exemplary lead design results in a temperature rise approximately four degrees less than that of a standard lead at a ring electrode.

Figure 7:
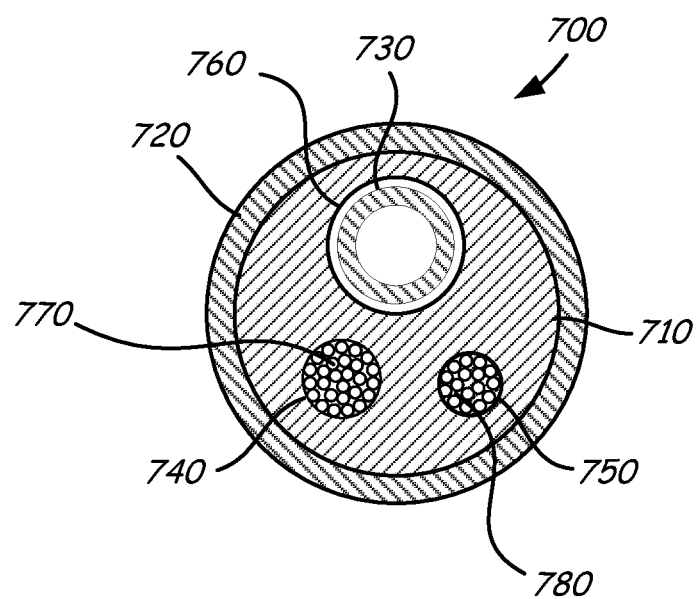
FIG. 7 is a transverse cross-sectional view of a lead with a multi-lumen construction that may be used in some embodiments of the present invention.

Although the embodiments above describe and illustrate multi-conductor leads with co-axially configured coil conductors, the high inductance conductor coils 320, 340 can advantageously be employed in other lead configurations within the scope of the present invention. For example, FIG. 7 illustrates a transverse cross-sectional view of an alternative embodiment of the lead 150 utilizing a multi-lumen lead body such as is commonly employed in conventional defibrillation leads. As shown in FIG. 7, the lead body includes an inner tubular member 710 and an outer tubular member 720 disposed over and bonded to the inner tubular member 710. The tubular members 710, 720 can be made from any number of flexible, biocompatible insulative materials, including without limitation, polymers such as silicone and polyurethane, and copolymers thereof. As further shown, the inner tubular member 710 includes a plurality of lumens 730, 740, 750, and conductors 760, 770, and 780 are disposed, respectively, in the lumens 730, 740, and 750. Each of the conductors 760, 770, and 780 extends longitudinally within the respective lumen 730, 740, and 750, and is electrically coupled to an electrode (e.g., the electrodes 360 in FIG. 3) and also to an electrical contact of the connector assembly 310.

In addition, the inner tubular member 710 may include a greater or lesser number of lumens, depending on the particular configuration of the lead 150. For example, the inner tubular member 710 may include a greater number of lumens to house additional conductor wires and/or electrode coils within the lead 150 for supplying current to other shocking coils and/or pace/sense electrodes.

In the embodiment of FIG. 7, the conductor 760 is configured in substantially the same manner as the coil conductor 320 described above, and can operate as a low-voltage pace/sense circuit as described above. Accordingly, the conductor 760 advantageously has the same high-inductance characteristics described above with respect to the conductor 320. In the illustrated embodiment, the conductors 770, 780 are stranded-wire cable conductors which are well known in the art for use in high voltage applications, e.g., to supply defibrillation stimuli to high voltage shocking coils such as the shocking coil 330 in FIG. 3.

The various embodiments of the lead 150 described above, advantageously minimize induced currents in the lead conductors resulting from exposure to external MRI electromagnetic fields. This is in contrast to conventional ICD lead systems utilizing stranded cable conductors to transmit the shocking currents from the PG to the shocking electrodes. While such cable conductors provide excellent electrical performance for delivering anti-tachycardia therapy, stranded cable conductors also have a low impedance and thus are susceptible to generation of induced currents when exposed to an alternating electromagnetic field such as that present during an MRI scan. The high impedance conductor configurations for the lead 150 described above minimize the effects of MRI radiation while still providing suitable electrical performance for use in anti-tachycardia therapy applications.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical device lead comprising:
an inner conductor coil comprising one or more generally cylindrically wound filars, wherein the inner conductor coil is configured to have a first inductance value when the inner conductor coil is subjected to a range of radio frequencies; and
a multi-filar outer coil comprising two or more generally cylindrically wound filars radially surrounding at least a portion of the inner conductor coil, wherein the multi-filar outer coil is configured to have a second inductance value that is less than the first inductance value when the multi-filar outer coil is subjected to the range of radio frequencies.

2. The implantable medical device lead of claim 1, wherein a layer of insulation is disposed about at least a portion of the inner conductor coil.

3. The implantable medical device lead of claim 1, wherein the inner conductor coil has a unifilar construction.

4. The implantable medical device lead of claim 1, wherein the inner conductor coil has an average pitch of approximately 0.005 inches.

5. The implantable medical device lead of claim 4, wherein the inner conductor coil has a unifilar construction and a mean coil diameter of 0.023 inches.

6. The implantable medical device lead of claim 1, wherein the inner conductor coil has an inductance greater than approximately 0.5 µH/inch.

7. The implantable medical device lead of claim 1, wherein the first inductance value (L) is set by a number of cylindrically wound filars (N), a pitch (b) of the inner conductor coil, and a mean coil diameter (a) by the equation $$L \approx \frac{\mu_0 \pi a^2}{4b^2 N^2}$$

where $\mu_0$ is the permeability of the free space.

8. The implantable medical device lead of claim 1, wherein the inner conductor coil has a DC resistance less than 200 ohms.

9. The implantable medical device lead of claim 1, wherein the multi-filar outer coil is a ribbon-type conductor coil.

10. A medical lead, comprising:
a flexible body having a proximal region with a proximal end, and a distal region;
a connector coupled to the proximal end of the body configured for electrically and mechanically connecting the lead to an implantable pulse generator;
an inner conductor coil configured to convey electrical signals between a distal section and a proximal section of the lead, the low voltage inner conductor coil comprising one or more generally cylindrically wound filars, wherein the inner conductor coil is configured to have a first inductance value when subjected to radio frequencies between 40 megahertz (MHz) and 300 MHz; and
a multi-filar outer conductor coil comprising two or more generally cylindrically wound filars radially surrounding at least a portion of the low voltage inner conductor coil, wherein the multi-filar outer conductor coil is configured to have a second inductance value when subjected to the radio frequencies between 40 megahertz (MHz) and 300 MHz, and wherein the second inductance value is less than the first inductance value.

11. The medical lead of claim 10, and further comprising:
a tri-filar shocking coil with a proximal end, wherein the proximal end of the tri-filar shocking coil is connected via a coupler to a distal end of the multi-filar outer coil.

12. The medical lead of claim 11, wherein the multi-filar outer coil has an outer diameter larger than an outer diameter of the tri-filar shocking coil.

13. The medical lead of claim 10, wherein the multi-filar outer conductor comprises a quad-filar coil having a helix-like shape.

14. The medical lead of claim 10, wherein the lead further includes one or more layers of insulating material surrounding one or both of the inner conductor coil and the multi-filar outer conductor coil.

15. The medical lead of claim 10, wherein the inner conductor coil and the multi-filar outer conductor coil have different pitches.

16. The medical lead of claim 10, wherein the inner conductor coil and the multi-filar outer conductor coil each have a pitch no greater than about 0.005 inch (0.127 mm).

17. An implantable medical device lead comprising:
an inner conductor coil comprising one or more wound filars and configured to have a first inductance value when subjected to radio frequencies between 40 megahertz (MHz) and 300 MHz;
a multi-filar outer conductor coil comprising two or more generally cylindrically wound filars radially surrounding at least a portion of the inner conductor coil, wherein the multi-filar outer conductor is configured to have a second inductance value when subjected to the radio frequencies between 40 megahertz (MHz) and 300 MHz, wherein the second inductance value is less than the first inductance value; and
a tri-filar shocking coil with a proximal end, wherein the proximal end is connected via a coupler to a distal end of the multi-filar outer conductor coil.

18. The implantable medical device of claim 17, wherein the inner conductor coil, the multi-filar outer conductor coil, and the tri-filar shocking coil have different pitches.

19. The implantable medical device of claim 17, wherein the lead further includes one or more layers of insulating material surrounding one or more of the low voltage inner conductor coil, the multi-filar high voltage outer conductor coil, and the tri-filar shocking coil.

20. The implantable medical device of claim 17, wherein a pitch of the multi-filar outer conductor coil is about 0.010 inches, a mean coil diameter of the multi-filar outer conductor coil is about 0.090 inches and results in a coil inductance value of about 0.13 µH/inch, and a pitch of the inner conductor coil is about 0.005 inches, the inner conductor coil is formed from one cylindrically wound filar, and a mean coil diameter of the inner conductor coil is about 0.023 inches resulting in a coil inductance per unit length value of about 0.5 µH/inch.

* * * * *